(12) United States Patent
Angelsen

(10) Patent No.: US 11,209,530 B2
(45) Date of Patent: Dec. 28, 2021

(54) METHOD FOR IMAGING OF NONLINEAR INTERACTION SCATTERING

(71) Applicant: Surf Technology AS, Trondheim (NO)

(72) Inventor: Bjørn Angelsen, Trondheim (NO)

(73) Assignee: SURF TECHNOLOGY AS, Trondheim (NO)

( * ) Notice: Subject to any disclaimer, the term of this patent is extended or adjusted under 35 U.S.C. 154(b) by 538 days.

(21) Appl. No.: 15/535,151

(22) PCT Filed: Dec. 10, 2015

(86) PCT No.: PCT/GB2015/053775
§ 371 (c)(1),
(2) Date: Jun. 12, 2017

(87) PCT Pub. No.: WO2016/092305
PCT Pub. Date: Jun. 16, 2016

(65) Prior Publication Data
US 2017/0343656 A1    Nov. 30, 2017

(30) Foreign Application Priority Data

Dec. 10, 2014 (GB) ...................... 1421936

(51) Int. Cl.
*G01S 7/52* (2006.01)
*G01S 15/89* (2006.01)
(Continued)

(52) U.S. Cl.
CPC ...... *G01S 7/52038* (2013.01); *G01S 15/8929* (2013.01); *G01S 15/8952* (2013.01);
(Continued)

(58) Field of Classification Search
CPC ........ G01S 7/52; G01S 15/89; G01S 7/52038; G01S 15/8929; G01S 15/8952; G01S 7/41; G01S 7/4802; A61B 5/0059
See application file for complete search history.

(56) References Cited

U.S. PATENT DOCUMENTS 5,623,928 A * 4/1997 Wright ................ G01S 7/52023
600/447
5,793,701 A * 8/1998 Wright ................ G01S 7/52023
367/11

(Continued)

FOREIGN PATENT DOCUMENTS

CN 101262960 A 9/2008
CN 2012035312 A2 8/2013
(Continued)

OTHER PUBLICATIONS

Chinese First Office Action and Search Report for corresponding Chinese Patent Application No. 2015800755822 and English Translation, dated Jan. 22, 2020.

Primary Examiner — Yuqing Xiao
Assistant Examiner — Amie M Ndure
(74) Attorney, Agent, or Firm — Browdy and Neimark, P.L.L.C.

(57) ABSTRACT

$1^{st}$ and $2^{nd}$ pulsed waves (103, 104) with $1^{st}$ and $2^{nd}$ center frequencies are transmitted along $1^{st}$ and $2^{nd}$ transmit beams so that the $1^{st}$ and $2^{nd}$ pulsed waves overlap at least in an overlap region (Z) to produce nonlinear interaction scattering sources in said region. The scattered signal components from at least the nonlinear interaction scattering sources are picked up by a receiver (102) and processed to suppress other components than said nonlinear interaction scattered signal components, to provide nonlinear interaction measurement or image signals. At least a receive beam is scanned in an azimuth or combined azimuth and elevation (Continued)

direction to produce 2D or 3D images of said nonlinear interaction scattering sources.

24 Claims, 6 Drawing Sheets

(51) Int. Cl.
    *A61B 5/00*           (2006.01)
    *G01S 7/41*           (2006.01)
    *G01S 7/48*           (2006.01)

(52) U.S. Cl.
    CPC ............... *A61B 5/0059* (2013.01); *G01S 7/41* (2013.01); *G01S 7/4802* (2013.01)

(56) References Cited

U.S. PATENT DOCUMENTS

| | | | |
|---|---|---|---|
| 7,727,156 B2 * | 6/2010 | Angelsen | B06B 1/064 |
| | | | 600/459 |
| 9,291,493 B2 | 3/2016 | Angelsen et al. | |
| 2009/0067458 A1 * | 3/2009 | Ji | H01S 3/0057 |
| | | | 372/25 |
| 2009/0178483 A1 * | 7/2009 | Angelsen | G01S 7/52077 |
| | | | 73/597 |
| 2010/0036244 A1 * | 2/2010 | Angelsen | G01S 15/8952 |
| | | | 600/438 |
| 2012/0050750 A1 * | 3/2012 | Hays | G01S 17/003 |
| | | | 356/519 |
| 2012/0169053 A1 * | 7/2012 | Tchoryk, Jr. | G01W 1/02 |
| | | | 290/44 |
| 2012/0194549 A1 * | 8/2012 | Osterhout | G02B 27/0093 |
| | | | 345/633 |
| 2012/0235884 A1 * | 9/2012 | Miller | G02B 27/0093 |
| | | | 345/8 |
| 2012/0274937 A1 * | 11/2012 | Hays | G01S 17/58 |
| | | | 356/337 |
| 2012/0288114 A1 * | 11/2012 | Duraiswami | H04R 1/406 |
| | | | 381/92 |
| 2013/0314694 A1 * | 11/2013 | Tchoryk, Jr. | G01N 21/45 |
| | | | 356/28.5 |
| 2015/0287422 A1 * | 10/2015 | Short | G01S 7/288 |
| | | | 704/205 |

FOREIGN PATENT DOCUMENTS

| | | |
|---|---|---|
| CN | 104125801 A | 10/2014 |
| WO | 2012035312 A2 | 3/2012 |

\* cited by examiner

METHOD FOR IMAGING OF NONLINEAR INTERACTION SCATTERING

FIELD OF THE INVENTION

The present invention addresses imaging of nonlinear scattering with elastic and electromagnetic waves and combinations of these. It has applications both in medical and technical fields.

BACKGROUND OF THE INVENTION

Material properties for both electromagnetic (EM) and elastic (EL) waves often show nonlinear properties where the material parameters depend on the amplitude of the field variables of the waves. Spatial variation in nonlinear material properties provide nonlinear scattering of both EM and EL waves, and imaging of such nonlinear scattering sources are in many situations useful to identify material properties. Both the forward wave propagation and local scattering of both EM and EL waves have mathematical similarities, and methods and instrumentation for imaging therefore have similar structures. Examples of uses of EL waves are material testing both with shear waves and compression waves, ultrasound medical imaging with compression waves, and SONAR sub-sea and geological measurements. EM waves have similar uses, where particularly new developments of EM technology in the high GHz and the THz range with wave lengths in the 0.1-1 mm range are being developed for medical imaging providing added information to the ultrasound images. EM imaging in the infra-red and optical frequency ranges also provides useful information both for material testing and medical imaging.

The nonlinear scattering can for both EM and EL waves be separated into a parametric and a resonant scattering type. For EL waves, the parametric scattering originates from a nonlinear variation of the local elasticity parameters with the amplitude of the local elastic wave field, where spatial variations of the nonlinear variation produce the nonlinear scattering. For EM waves, the parametric scattering originates from a nonlinear variation of the local dielectric constant or magnetic permeability with the amplitude of the local EM wave field, where spatial variations of the nonlinear variation produce the nonlinear scattering. With elastic compression waves, referred to as acoustic waves, one for example gets strong nonlinear parametric scattering at the interface between soft materials and hard materials, for example as found with ultrasound nonlinear scattering from micro calcifications in soft tumor tissue, or acoustic scattering from hard objects in soil like mines or other objects. One also gets strong nonlinear scattering at the interface between harder materials and much softer materials, for example as found with ultrasound scattering from gas micro-bubbles in blood or gas filled swim-bladders of fish and the like in water, or acoustic scattering from cracks in for example polymers, polymer composites, rocks or metal parts.

With a single frequency band incident wave, the parametric nonlinear scattering produces harmonic components of the incident frequency band in the scattered wave. With dual band incident waves that interact locally, the parametric nonlinear scattering produces bands around convolutions of the incident frequency bands, which provide bands around sums and differences of the incident frequencies. However, the nonlinear variation of the material parameters also produces an accumulative nonlinear distortion of the forward propagating wave. When the pulse length of the high frequency pulse increases above approximately a half period of the low frequency pulse, the linear scattering from the nonlinear forward propagation distortion has a similar signature to the local nonlinear scattering, and it is in this case difficult to distinguish the signal components that occur from linear scattering of the nonlinear forward propagation distortion of the incident wave, and the signal components that occur from local nonlinear scattering. The present invention presents solutions in the form of methods and instrumentation that suppresses the components that originate from strong linear scattering of components produced by nonlinear forward propagation distortion and extracts the local nonlinear scattering components to produce a spatial imaging of the local nonlinear scattering sources.

Resonant nonlinear scattering has a time lag involved, which in some situations can be used to separate signal components from local nonlinear scattering and forward propagation distortion of the incident waves. However, the current invention provides further advantages for imaging of local resonant nonlinear scattering sources.

For acoustic waves, gas micro-bubbles show resonant scattering, for example, where the resonance originates from the energy exchange between the nonlinear elasticity of the bubble with shell and gas, and a co-oscillating fluid mass around the bubble with a volume approximately 3 times the bubble volume. As both the elasticity and the mass vary with bubble compression, the resonance frequency is nonlinearly affected by the incident acoustic wave field, producing a particularly strong nonlinear scattering with a large amount of harmonic components of the incident frequency (n-times the incident frequency) and even sub-harmonic components of the incident frequency (a fraction of the incident frequency) in the scattered field, and supra-harmonic components (bands around the harmonic components) of the incident frequency. However, for imaging at frequencies well above the bubble resonance frequency, the nonlinear scattering is much lower, and the present invention provides solutions for enhanced imaging of micro-bubbles at frequencies above the resonance frequency.

Micro-calcifications can also produce resonant scattering of an acoustic wave at low frequencies, where the calcium particle that is heavier than the surrounding tissue interacts with the shear elasticity of the surrounding tissue to produce a low resonance frequency. The dual frequency solution of this invention, where the frequency of the manipulation wave is low, can excite this resonance when the calcium particles are small.

Resonant nonlinear EM scattering originates in the interaction between the wave field and the atoms and molecules, which is best described within the realm of quantum physics. Examples of EM resonant scattering are fluorescence which has similarities to sub-harmonic acoustic scattering. Two-photon quantum scattering is similar to $2^{nd}$ harmonic parametric scattering, but includes detailed dynamics with time lags in the process.

There is also found a nonlinear interaction between EM and EL waves in materials, where for example EL compression waves change the EM material parameters in the process called the acousto-optic effect. Absorption of EM waves in materials produces a radiation force and local heating of the material that generates acoustic waves in a process called the photo-acoustic effect. The invention hence addresses both EM and EL waves, and combinations of these, where the waves referred to in the description and claims can be EM and/or EL waves.

SUMMARY OF THE INVENTION

This summary gives a brief overview of components of the invention and does not present any limitations as to the extent of the invention, where the invention is solely defined by the claims appended hereto.

The invention operates with both acoustic and electromagnetic arrays, and combinations of these, for example with the photo-acoustic principle. The general principle of the invention is described using acoustic waves as an example, where the transition to electromagnetic waves can be done by anyone skilled in the art.

$1^{st}$ and a $2^{nd}$ pulsed waves are transmitted in at least one transmit event along $1^{st}$ and $2^{nd}$ transmit beams in skewed or opposite directions into an object, where the $1^{st}$ and $2^{nd}$ transmitted pulses overlap in space and time in a nonlinear interaction overlap region of the object at an angle θ between the forward propagation directions of the beams where θ is any angle in the interval of 160-200 deg. For objects where the parameters for wave scattering and propagation depends on the amplitude of the wave-field, one obtains nonlinear interaction scattering sources in the overlap region, with frequency components that are sums and differences of the frequency components of the $1^{st}$ and $2^{nd}$ pulsed waves. The nonlinear interaction scattered components are picked up by a receive array, that can be one of the transmit arrays, or a separate array, and through processing one can separate the nonlinear interaction scattered components from other receive components either through i) filtering in the time domain, or ii) through pulse inversion techniques where one transmits two events of $1^{st}$ and $2^{nd}$ pulsed waves with differences in the polarity, amplitude, or frequency of one of the $1^{st}$ and $2^{nd}$ pulsed waves and combining the receive signals from both transmit events, or iii) a combination of filtering and pulse inversion.

For opposite propagating $1^{st}$ and $2^{nd}$ transmit waves, the depth location of the overlap region is determined by the relative timing of the transmit of the $1^{st}$ and $2^{nd}$ pulsed waves. The length of the overlap region is determined by the length of the pulses, where one generally would choose a short pulse of one of the transmit pulses (sensing pulse) for good spatial image resolution, and the other pulse (manipulation pulse) can be relatively long to determine the length of the overlap region. However, the strength of the nonlinear interaction scanning increases with the amplitude of the two transmitted pulses, and with longer pulses absorption heating of the transducer array and object limits the pulse amplitude, hence reducing the strength of the nonlinear interaction scanning. It is in this situation an advantage to use as low frequency of say the $1^{st}$ pulse (manipulation pulse) as possible given allowable aperture dimensions and beam diffraction broadening with depth, while the other pulse has high frequency for strong scattering and spatial resolution. The current invention presents solutions for such a system.

The invention also claims an instrument that operates according to the methods. The instrument and methods can operate with different types of arrays, for example at least two linear or phased arrays, or a ring array, all known in the art.

DETAILED DESCRIPTION OF THE PREFERRED EMBODIMENTS OF THE INVENTION

Figure 1:
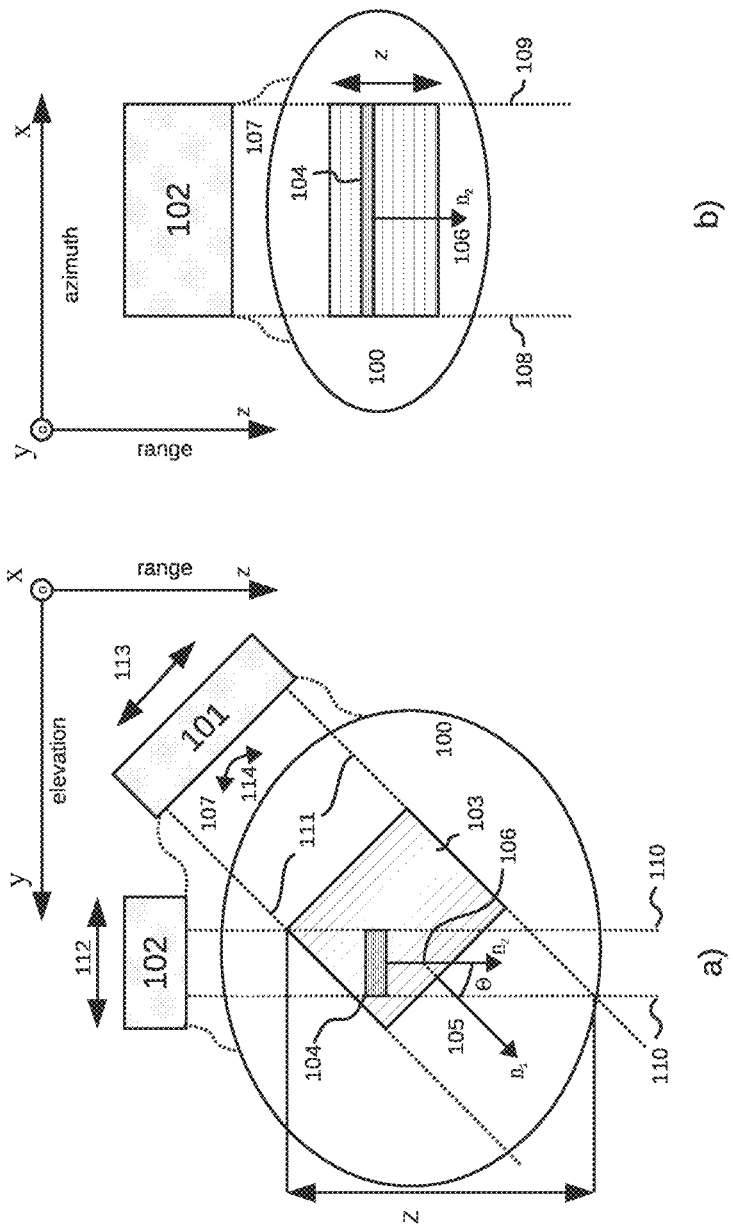
FIG. 1 illustrates arrangement of arrays and beams for imaging of nonlinear interaction between two beams.

We will here give examples of embodiments according to the invention. The description does not present any limitations as to the extent of the invention, where the invention is solely defined by the claims appended hereto.

We use acoustic pressure waves in an object with $2^{nd}$ order elasticity as an example for description of the invention. It will however be clear to anyone skilled in the art how this example can be extended to more complex elasticity situations, for example the situation of resonant nonlinear scatterers, the use of acoustic shear waves, acoustic plate waves, acoustic surface waves, sand also electromagnetic waves. Cracks in polymers, polymer composites, or rocks, provide especially strong nonlinear scattering. Methods according to the current invention can for example be used to detect cracks in rocks to assess stability of formations, problems with inflow of water in tunnels, and also assessment of the neighborhood of oil and gas wells. For plates of polymer or polymer composites in constructions in for example airplanes, vessels or windmills, one can for example use the methods of detecting nonlinear interaction scattering according to this invention to detect cracks or other damages in the material both as quality control in manufacturing, and for surveillance of safe operation of constructions. For plates one can conveniently use surface, or plate mode elastic waves, or pressure waves, or a combination of these.

For the illustrative example of pressure waves, the volume compression δV of a small volume element ΔV by a pressure p, can to the $2^{nd}$ order in the pressure be written as $\delta V/\Delta V = -\nabla \psi = (1-\beta_n \kappa p)\kappa p$, where ψ is the particle displacement in the wave, κ is the linear compressibility, and $\beta_n$ is a nonlinearity parameter. With this nonlinear elasticity we get a wave equation that includes nonlinear forward propagation and scattering phenomena as $$\underbrace{\nabla^2 \varphi(r, t) - \frac{1}{c_0^2(r)} \frac{\partial^2 \varphi(r, t)}{\partial t^2}}_{(1)Linear\ propagation} + \quad (1)$$

$$\underbrace{\frac{2\beta_p(r)p(r, t)}{c_0^2(r)} \frac{\partial^2 \varphi(r, t)}{\partial t^2}}_{(2)Nonlinear\ propagation} - \underbrace{h_p(r, t) \underset{t}{\otimes} \frac{1}{c_0^2} \frac{\partial^2 \varphi(r, t)}{\partial t^2}}_{(3)Absorption} =$$

-continued $$\underbrace{\frac{\sigma_l(\underline{r})}{c_0^2(\underline{r})}\frac{\partial^2 \varphi(\underline{r},t)}{\partial t^2} + \nabla(\gamma(\underline{r})\nabla \varphi(\underline{r},t))}_{\text{(4)Linear scattering source terms}} - \underbrace{\frac{2\sigma_n(\underline{r})p(\underline{r},t)}{c_0^2(\underline{r})}\frac{\partial^2 \varphi(\underline{r},t)}{\partial t^2}}_{\text{(5)Nonlinear scattering source term}}$$

where $\underline{r}$ is the space coordinate vector, t is time, $\varphi(\underline{r},t)$ is the acoustic impulse momentum field defined through $\rho(\underline{r})\underline{u}(\underline{r},t) = -\nabla\varphi(\underline{r},t)$ where $\underline{u}(\underline{r},t) = \partial\underline{\psi}(\underline{r},t)/\partial t$ is the acoustic particle velocity, $\rho(\underline{r})$ is the object mass density, and $p(\underline{r},t) = \partial\varphi(\underline{r},t)/\partial t$ is the acoustic pressure field. $c_0(\underline{r})$ is the linear wave propagation velocity for low field amplitudes, $\beta_p(\underline{r}) = \beta_n(\underline{r})\kappa(\underline{r})$ is a nonlinear propagation parameter, $h_p(\underline{r},t)$ is a convolution kernel that represents absorption of wave energy to heat. $\sigma_l(\underline{r})$ and $\gamma(\underline{r})$ are the relative rapid (on a scale<approximately the wave length) spatial variations of the compressibility and mass density of the object that gives linear scattering parameters, and $\sigma_n(\underline{r})$ is a nonlinear scattering parameter. The left side propagation parameters vary with $\underline{r}$ on a scale>approximately the wavelength, while the right side scattering parameters vary with $\underline{r}$ on a scale<approximately the wave length. A similar equation for electromagnetic waves can be formulated that represents similar nonlinear propagation and scattering phenomena for the EM waves.

The different terms of Eq. (2) have different effects on the wave propagation and scattering: The linear propagation terms (1) guide the linear forward propagation of the incident wave without producing new frequency components. The linear scattering source terms (4) produce local scattering of the forward propagating wave without producing new frequency components in the scattered wave. More detailed analysis shows that the nonlinear propagation term (2) modifies the propagation velocity through a combination of term (1+2) as $$c(r,p) = \sqrt{\frac{c_0^2(r)}{1 - 2\beta_p(r)p(r,t)}} = \frac{c_0(r)}{1 - \beta_p(r)p(r,t)} \quad (2)$$

where we in the last approximation have used that $|2\beta_p(\underline{r})p_1(\underline{r},t)| = |x| \ll 1$ which allows the approximation $\sqrt{1-2x} \approx 1-x$. The nonlinear variation of the propagation velocity with the pressure p in Eq. (2) arises from that a high positive pressure makes the material stiffer with a corresponding increase in propagation velocity, while a high negative pressure makes the material softer with a corresponding decrease in propagation velocity. This produces a forward propagation distortion of the wave, well known in nonlinear wave propagation. The propagation time $t(\underline{r}_1,\underline{r}_2)$ of a field point at $(\underline{r}_1,t_1)$ of the wave to $(\underline{r}_2,t_2)$ is in the geometric ray propagation approximation given as $$t(r_1, r_2) = \int_{\Gamma(r_1,r_2)} \frac{ds}{c(r,p)} = \quad (3)$$

$$\int_{\Gamma(r_1,r_2)} \frac{ds}{c_0} - \int_{\Gamma(r_1,r_2)} \frac{ds}{c_0}\beta_p(s)p(s) = t_0(r_1,r_2) + \tau(r_1,r_2)$$

$$t_0(r_1,r_2) = \int_{\Gamma(r_1,r_2)} \frac{ds}{c_0} \quad \tau(r_1,r_2) \int_{\Gamma(r_1,r_2)} \frac{ds}{c_0}\beta_p(s)p(s)$$

where $\Gamma(\underline{r}_1,\underline{r}_2)$ is the geometric ray propagation path from $\underline{r}_1$ to $\underline{r}_2$, p(s) is the wave pressure at the field point as a function of propagation, $t_0(\underline{r}_1,\underline{r}_2)$ is the propagation time in the low amplitude linear regime, and $\tau(\underline{r}_1,\underline{r}_2)$ is the nonlinear modification of the propagation time which we denote the nonlinear propagation delay.

Hence, for materials with adequately high nonlinearity in the material parameters relative to the wave field amplitude, the nonlinearity affects both the propagation velocity and local scattering of the wave. A slowly varying (close to constant on a scale>~wave length) of the nonlinear material parameters will provide a nonlinear forward propagation distortion of the incident waves that accumulates/increases in magnitude with propagation distance through term (2) of Eq. (1). A rapid oscillation (on a scale<~wavelength) of the nonlinear material parameters produces a local nonlinear scattering of the incident waves through term (5) of Eq. (1).

The nonlinear propagation (2) and scattering (5) phenomena are in the $2^{nd}$ order approximation of material parameters are both proportional to $2p\ddot{\varphi}=2p\dot{p}=\partial p_p^2/\partial t$. For a wave that is a sum of two components $p=p_1+p_2$ as in our example, the nonlinear propagation and scattering are both given by $$\sim p(r,t)^2 = \quad (4)$$

$$(p_1(r,t) + p_2(r,t))^2 = \underbrace{p_1(r,t)^2}_{\text{nonlin self distortion}} + \underbrace{2p_1(r,t)p_2(r,t)}_{\text{nonlin interaction}} + \underbrace{p_2(r,t)^2}_{\text{nonlin self distortion}}$$

A multiplication of two functions in the temporal domain produces a convolution of the functions temporal Fourier transforms (i.e. temporal frequency spectra) in the temporal frequency domain. This convolution introduces frequency components in the product of the functions that are sums and differences of the frequency components of the factors of the multiplication. For the nonlinear self distortion terms, this produces harmonic and sub-harmonic components of the incident frequency bands.

FIG. 1 shows a transducer array and beam structure of one example embodiment for measurement or imaging of nonlinear interaction scattering of an object 100 according to the invention. FIG. 1a shows the structure in the elevation direction, and FIG. 1b shows the structure in an azimuth direction (normal to the elevation direction) of the beams. The Figure further shows a $1^{st}$ transducer array 101 transmitting a $1^{st}$ pulsed wave beam 103, $p_1(\underline{r},t)$, that propagates in the direction 105 indicated by the unit vector $\underline{n}_1$ and is termed manipulation wave in the following. The Figure further shows a $2^{nd}$ ultrasound transducer array 102 transmitting a $2^{nd}$ pulsed wave beam 104, $p_2(\underline{r},t)$, that propagates in the direction 106 indicated by the unit vector $\underline{n}_2$ and is termed sensing wave in the following. 107 indicates potential wave coupling material between the transducers and the object, for example water or a coupling gel. In the elevation plane there is an angle $\theta$ between the beam directions 106 and 105. The manipulation pulsed wave beam 103 is fairly wide in the transverse elevation plane, and correspondingly long, so that it determines an overlap region between the two pulsed wave beams in a selected depth interval Z where $p_1p_2$ will be different from zero and hence produce nonlinear interaction scattering sources. For low frequencies $f_1$ of $p_1$ it is advantageous with a certain width of the pulse 103 to limit effects of diffraction. This width also increases the width of the overlap region, provided a matched length of the pulse 103. We should note that long pulses might require reduced pulse amplitudes due to absorption heating, which reduces the strength of the nonlinear interaction scattering $\sim p_1p_2$, making an advantage to use short and focused pulses. The length Z of the overlap region can be increased through lateral scanning of the pulsed beam 103, for example through rotation or lateral movement of the array 101 indicated by the arrows 113 and 114, or a combination of both.

Figure 6:
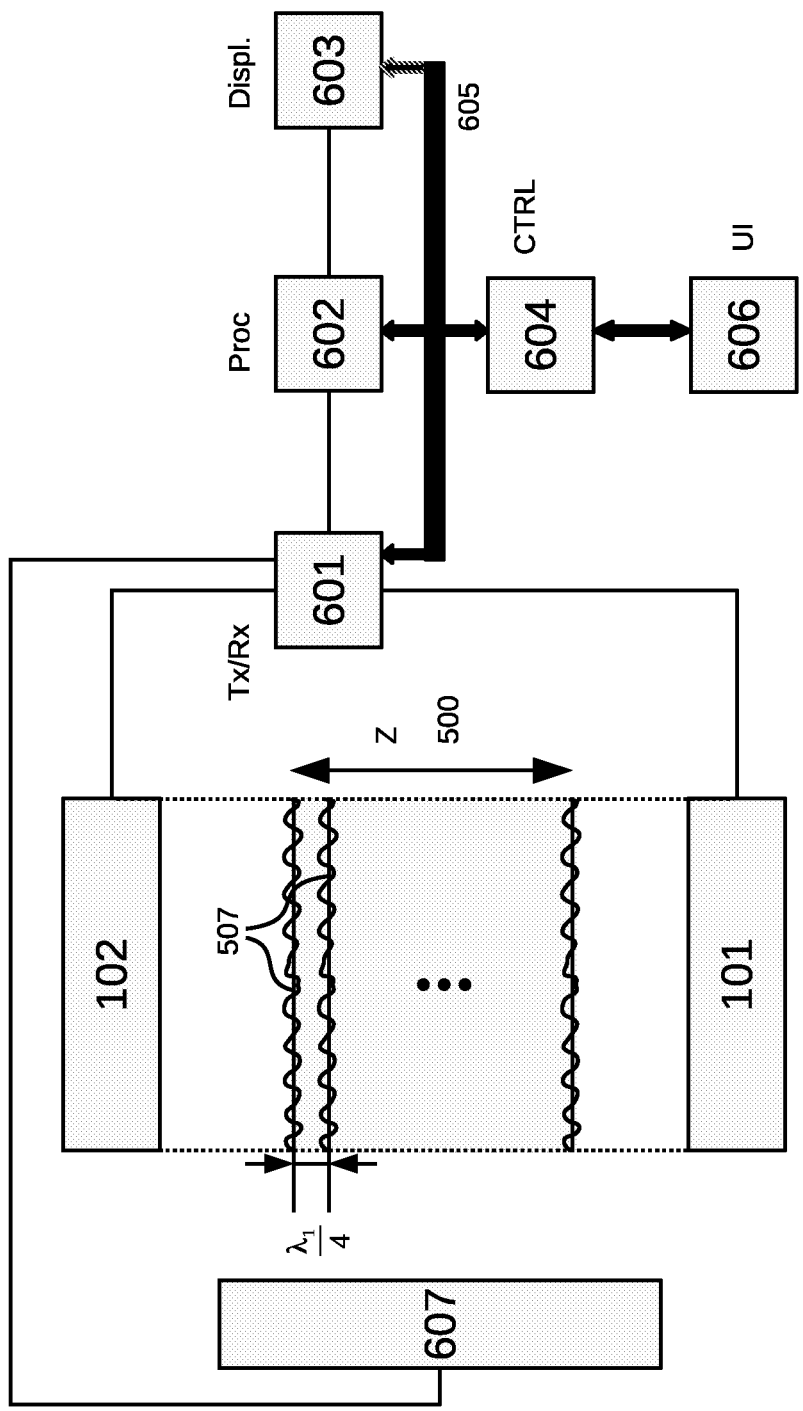
FIG. 6 illustrates a block diagram of an instrument according to the invention.

The nonlinear scattering source term (5) in Eq. (1) is a monopole scattering term that fundamentally scatters equally in all directions from sources smaller than a wavelength of the incident waves. Interference between neighboring scatterers and scatterers much larger than the wave length will however produce a direction dependent scattering. In this example the scattered signal is received with the array 102, while in FIG. 6 is also illustrated an example $3^{rd}$ array 607 for reception of the scattered signal. For lateral resolution in the image, the receive array can be divided into many small elements in the lateral direction, to obtain lateral azimuth receive resolution in the image according to known methods. Such element division also allows electronically steered transmit and receive focusing according to known methods. To obtain lateral resolution in the elevation direction one could according to known methods use a receive and transmit beam from array 102 that are narrow in the elevation direction, shown by the lines 110 in FIG. 1a. 3D imaging of the object can according to known methods for example be obtained by mechanically scanning the array structure in the elevation direction indicated by the arrows 112 in FIG. 1a. With a two-dimensional matrix receive array 102 one could obtain full electronic 3D scanning of narrow transmit/receive beams in the elevation direction, according to known methods. One could also for 3D scanning with a matrix array transmit a pulsed wave 104 that is wide in the elevation direction, and obtain 3D elevation resolution with the receive beams.

In this example both pulsed wave beams 103 and 104 are wide in the azimuth direction, FIG. 1b. Both beams are in this example for illustration purposes bounded by the same lines 108 and 109 in the azimuth plane, where in practice the boundaries of the two beams will be different due to different apertures and frequencies. The two other direction angles of the beams are in this example selected so that the overlap region between the $1^{st}$ an $2^{nd}$ pulses becomes parallel to the surface of the array 102, which is preferred in many set-ups. It is however clear to anyone skilled in the art that the two other relative direction angles between the beams can differ from what shown in FIGS. 1 and 4 in certain set-ups and still obtain the same effect for the same purposes according to the invention as claimed.

To transmit wide beams the array 101 could in principle be composed of a single transducer element, as receive resolution is obtained by the array 102. For simple electrical impedance matching to the transmitters to transmit high amplitudes, it is however convenient that the array is composed of several smaller elements. This also allows electronic focusing of the transmit pulse 103. Focusing of the transmit beams increases the transmitted pressure amplitudes $p_1$ and $p_2$, that increases the nonlinear scattering $\sim p_1 p_2$ in a selected depth region, also prefer multi-element arrays for transmit, albeit one can also use lenses, all according to known methods. Focusing of the transmit beams require lateral azimuth scanning of the focused transmit beams for 2D or 3D imaging, according to known methods.

Figure 3:
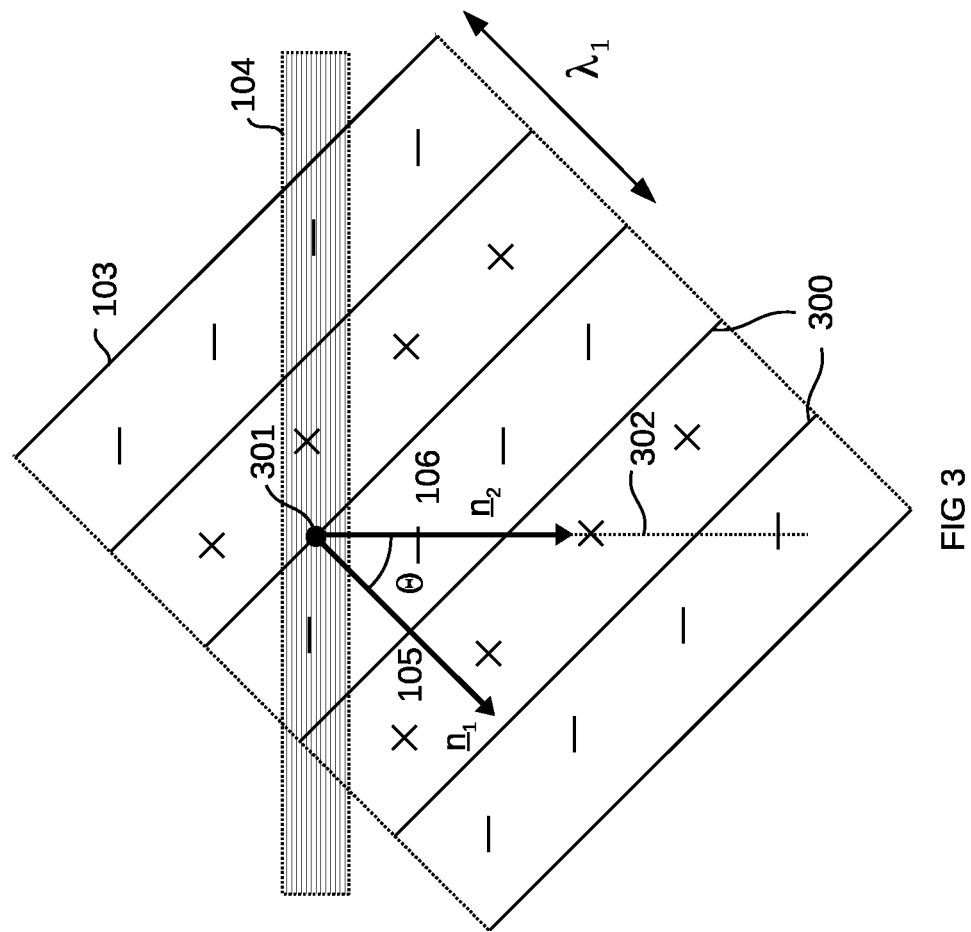
FIG. 3 further illustrates the propagation interaction of two waves at an angle to each other.

During a time interval $\Delta t$, both waves propagate a distance $c \Delta t$. FIG. 3 illustrates in the elevation direction the manipulation pulse 103 at a starting time t, propagating in the direction of the unit vector $\underline{n}_1$, where the lines 300 indicates zero fronts of the wave and the ±'es indicates the positive and negative swings of the pressure oscillation at time t. The sensing pulse is also illustrated as 104 at this starting time t, propagating in the direction of the unit vector $\underline{n}_2$. We select $c\Delta T$ so that a peak amplitude 301 of the sensing pulse 104 moves backwards one wavelength $\lambda_1$ on the manipulation pulse 103 in the combined propagation of 103 and 104. The point 301 then propagates forward a distance $c\Delta T\underline{n}_2$. The phase of the wave 103 at the path of the field point 301 then changes as $\omega_1(\Delta T - \underline{n}_1 c\Delta T\underline{n}_2/c) = \omega_1(1-\underline{n}_1\underline{n}_2)\Delta T$ which is set equal to $\omega_1 T_1$ for one wave length propagation along 103, where $T_1=1/f_1$ is the period of the $1^{st}$ pulse 103. This gives $$\Delta T = \frac{T_1}{1-\underline{n}_1\underline{n}_2} = \frac{T_1}{1-\cos\theta} \quad (5)$$

where $\theta$ is defined above and in the Figure. For $\theta \to 0$ both pulses 103 and 104 get the same propagation direction and $\Delta T \to \infty$, which implies that the phase between the peak of pulse 104 and the oscillation of 103 is constant along their common propagation direction, i.e. pulse 104 surfs on the pulse 103. The polarity of p(s) in Eq. (3) is then constant, and $\tau(z)$ in Eq. (3) represents an accumulative increase in magnitude of the nonlinear propagation delay of pulse 104 with depth, which must be accounted for in the signal processing. For $\theta = \pi/2$ the pulse 103 propagates at right angle to the pulse direction of 104, and we get $\Delta T = T_1$, and for $\theta = \pi$ the pulse 103 propagates in the opposite direction of the pulse 104, and we get $\Delta T = T_1/2$.

For $\theta_1 < \theta < 2\pi-\theta_1$ where $0 < \theta_1 < \pi/2$ the pressure p(s) of the manipulation pulse 103 at the location of the sensing pulse 104, p(s) included in the integral for the nonlinear propagation delay $\tau$ in Eq. (3), will oscillate in polarity with a limited amplitude in the propagation of the pulses, and so will also $\tau$. A typical value for $\beta_p \sim 2\cdot 10^{-9}$ Pa$^{-1}$. For a peak pressure of the manipulation pulse of P=1 MPa the maximal value of r becomes from Eq. (3) for $f_1$=0.5 MHz, $T_1=1/f_1$ and $\omega=2\pi f_1$ $$\frac{\tau_{max}}{T_2} \sim \frac{\beta_p P}{T_2}\int_0^{T_1/2}dt\sin\frac{2\pi t}{T_1} = \frac{\beta_p P}{\pi}\frac{1}{1-\cos\theta}\frac{T_1}{T_2} \sim (4.3, 1.3, 0.6)\cdot 10^{-2} \quad (6)$$

where we have chosen $\theta$=(45, 90, 180) deg and $T_2$=100 ns corresponding to a frequency $f_2=1/T_2$=10 MHz of the sensing pulse 104. This gives $\tau_{max}\sim$(4.3, 1.3, 0.6)ns which could conveniently be corrected for for low values of $\theta$ or high values of P, for maximal suppression of non-interacting terms in the received signal.

We define two groups of nonlinear distortion terms in the received signal:

Group A originates from the linear scattering, i.e. term (4) of Eq. (1), of the forward accumulative nonlinear propagation distortion components in the incident wave, i.e. combination of term (1+2) and term (4) in Eq. (1). The self-distortion terms are always positive, and the harmonic distortion of the waves hence increases accumulatively with propagation depth, attenuated by absorption that increases with harmonic frequency, and geometric spread of the waves. For the nonlinear interaction term where the waves cross each other at an angle $\theta$, the nonlinear term of the propagation velocity in Eq. (2) will oscillate with propagation depth due to the oscillations in p(s) in Eq. (3), and with adequately large angle $\theta$ between the beams, the forward propagation distortion of this term is oscillatory and may be negligible for strong nonlinear interaction scattering terms.

Group B originates directly in the local nonlinear scattering of the incident waves, i.e. term (5), and is often be weaker than the Group A for terms where the forward nonlinear accumulation distortion is effective. With an adequately large angle $\theta$ between the $1^{st}$ and $2^{nd}$ incident waves the nonlinear forward distortion is low for the nonlinear interaction term Eqs. (5,6), but not for the self distortion terms, and this allows detection of the nonlinear interaction scattering with the current invention.

There is also in principle a Group C found as local nonlinear scattering from term (5) of the forward accumulative nonlinear propagation distortion components in the incident wave, i.e. interaction between term (1+2) and term (5) in Eq. (1), but typical nonlinear material parameters are so low that this group is negligible.

Figure 2A:
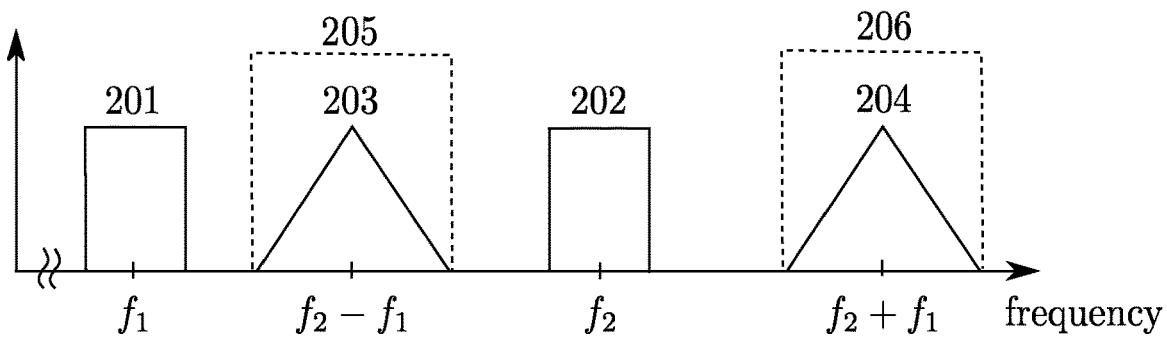
FIGS. 2a and 2b illustrates formation of sum and difference frequency bands of the incident $1^{st}$ and $2^{nd}$ transmitted temporal frequency bands, and extraction of the nonlinear interaction scattering signal through filtering in the temporal frequency domain.

FIG. 2a shows the temporal frequency spectra 201 and 202 of the incident pulsed waves 103 and 104. The temporal frequency spectra of the nonlinear interaction term $\sim 2p_1(\underline{r},t)p_2(\underline{r},t)$ is then the convolution of 201 and 202 shown as 203 and 204. When the incident frequency bands 201 and 202 are so arranged that there is no overlap with the nonlinear interaction scattered bands 203 and 204, as shown in FIG. 2a, one can suppress linearly scattered bands 201 and 202 to extract the nonlinear interaction scattered components by band pass filtering the receive signal in the temporal frequency domain, for example with the band pass filters 205 and 206 illustrated in FIG. 2a. To increase sensitivity to the nonlinear interaction scattering one can merge the outputs of both bands 203 and 204 in the forming of image signals.

We note that the harmonic bands of 201 and 202 are not shown in the Figure. In many situations one can get harmonic bands from self distortion components of the incident bands 201 or 202 that interferes with the nonlinearly interaction scattered bands 203 and 204, either through forward propagation distortion with linear scattering (Group A) or local nonlinear scattering (Group B), reducing the sensitivity to the nonlinear interaction scattering. Group A is generally the strongest, but Group B can also be strong with nonlinear resonant scatterers like ultrasound contrast agent microbubbles. One way to improve this situation is to use the method of pulse inversion where one transmits two pulse sets of $1^{st}$ and $2^{nd}$ pulses, changing the polarity of one of $p_1$ and $p_2$ for the $2^{nd}$ pulse set. The polarity of the scattered nonlinear interaction term $\sim 2p_1p_2$ will then change polarity for the $2^{nd}$ pulse set, while the even ($2^{nd}$, $4^{th}$, . . . ) harmonic self-distortion components $\sim p_1^2$ and $p_2^2$, for both Group A and Group B scattering, will not change polarity. Hence, subtracting the receive signals from these two transmit events in the method often referred to as pulse inversion, will then enhance the nonlinear interaction scattering term above even harmonic components of the incident bands. The transmitted pulse 103, $p_1$, will in the current example arrive at the receiving transducer 102 at the same time as the nonlinear interaction scattered signal. Changing the polarity of $p_2$ (104) in this pulse inversion process, will then suppress potential received components of $p_1$ in the received signal at 102. Linearly scattered components from the pulse $p_2$, which has changed polarity, at 102 will be enhanced in this process, and can be suppressed by filtering in the time domain.

Figure 2B:
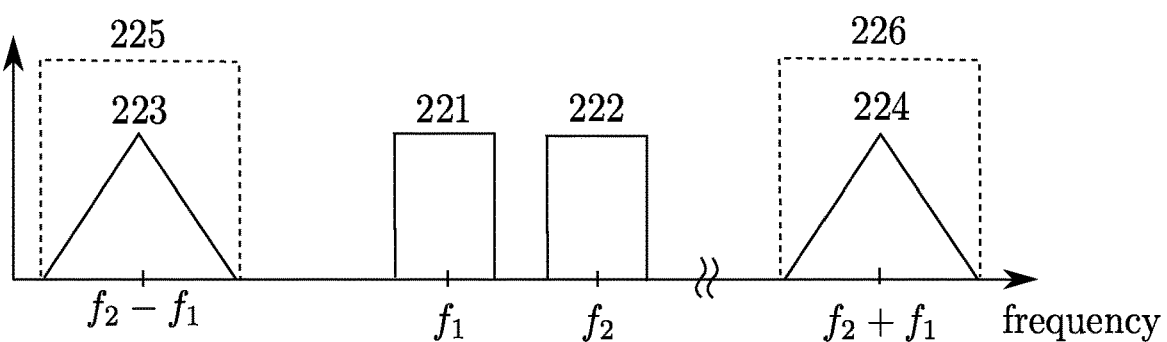

FIG. 2b shows a modification of the spectra in FIG. 2a where the transmitted spectra 221 around $f_1$ and 222 around $f_2$ are now so close that the nonlinear interaction convolved spectrum 223 around $f_2-f_1$ is found at frequencies well below the lower transmit band 221, while the nonlinear interaction convolved spectrum 224 around $f_1+f_2$ is found at frequencies close to twice the upper transmit band 222 frequency (i.e. close to $2^{nd}$ harmonic components of 222). The low frequency interaction scattered band 223 can be separated through band pass filtering with the filter 225 and the high frequency interaction scattered band 224 can be separated with the filter 226. One can also use a pulse inversion technique where for example the polarity of the high frequency transmit spectrum 222 is changed in the $2^{nd}$ transmit event. Band stop filtering around $f_2$ can then be used to remove the spectrum of 222 in the received signal. The reduced frequencies of the low nonlinear interaction scattering band 223 provide low absorption of this scattered band on receive and increase sensitivity to the nonlinear interaction scattering, while the low frequencies provide low lateral resolution with limited receive apertures. Variations of these schemes can be developed by anyone skilled in the art.

With a distance L between transducer array 101 and 102 the manipulation wave ($1^{st}$ wave) propagates a distance L-z to the interaction depth z, while the sensing wave ($2^{nd}$ wave) propagates a distance 2z back and forth to the interaction depth z. The frequency $f_2$ for the $2^{nd}$ wave $p_2$ (sensing wave) is chosen as high as possible to obtain adequate signal and best possible resolution for the depth range. To further improve sensitivity for the nonlinear interaction term $\sim 2p_1(\underline{r},t)p_2(\underline{r},t)$ for L-z large, it is useful to select the frequency $f_1$ of the $1^{st}$ wave $p_1$ (manipulation wave) as low as possible for low absorption, but adequately high to get an adequately collimated pulse 103, $p_1$. We call this the low frequency (LF) pulse. The high frequency (HF) $f_2$ is selected high to get adequate spatial resolution for the given imaging depth into the object, for example with the frequency ratio $f_1:f_2 \sim 1:3$-1:30. In particularly preferred embodiments the ratio is in the order of ~1:10. For ultrasound imaging one could for example in one application choose $f_2 \sim 10$ MHz to image down to 40 mm with $f_1 \sim 1$ MHz, or in another application choose $f_2 \sim 3.5$ MHz to image down to 150 mm with $f_1 \sim 0.3$ MHz, i.e. a frequency ratio of about 1:10. Similar examples are found for scattering of EM waves. For imaging of contrast agent micro-bubbles at frequencies $f_2$ well above the bubble resonance frequency, one would preferably choose $f_1$ below or around the resonance frequency, as the LF pulse 103 would then manipulate the bubble diameter.

Figure 2C:
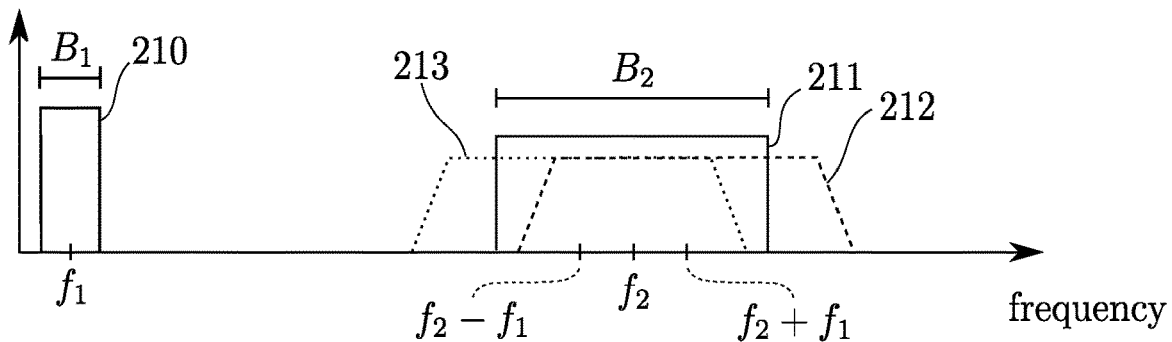
FIG. 2c illustrates formation of sum and difference frequency bands of the incident $1^{st}$ and $2^{nd}$ transmitted temporal frequency bands when the center frequency of the $1^{st}$ transmitted wave is less than the temporal frequency bandwidth of the $2^{nd}$ transmitted wave.

In FIG. 2c it is for this situation shown an example incident LF spectrum 210 for $p_1$ and an example incident HF spectrum 211 for $p_2$, with the convolved sum and difference frequency spectra as 212 and 213 from the nonlinear interaction product of $p_1$ and $p_2$ in Eq. (5). The center frequencies of 212 and 213 are $f_2+f_1$ and $f_2-f_1$, respectively. The sum and difference frequency spectra 212 and 213 overlap in this example with each other and the incident HF spectrum 211. In the convolution between the frequency spectra 210 and 211, one gets averaging of neighboring frequency components of the HF spectrum 211 over the bandwidth $B_1$ of the LF spectrum 210. This averaging also produces the skewed edges of the spectra 212 and 213. When the HF pulse is much shorter than the LF pulse, the frequency resolution in the HF spectrum 211 is wider than the bandwidth $B_1$ of 210 and this averaging has negligible effect on the sum and difference spectra 212 and 213, and allows the assumption of a continuous LF oscillation, i.e. infinitely long LF pulse in the analysis in Eq. (5).

FIG. 2c shows an example where there is considerable overlap between the sum and difference spectra 212 and 213 and the original HF spectrum 211. One can in this situation retrieve the Group B components from the received signal through the pulse inversion technique by using two transmit events of combined LF and HF pulse transmits, changing the polarity of the LF pulse $p_1$ for the $2^{nd}$ transmit event. The polarity of the scattered nonlinear interaction term (212 and 213) ~$2p_1p_2$ will then change polarity for the $2^{nd}$ transmit event, while the linearly scattered HF signal (211) does not. Subtracting the received signals from the two transmit events will then strongly suppress the linearly scattered HF signal (211) and extract the nonlinearly scattered HF signal (212 and 213). Even harmonic components of the LF pulse will also be suppressed in this process.

Figure 4:
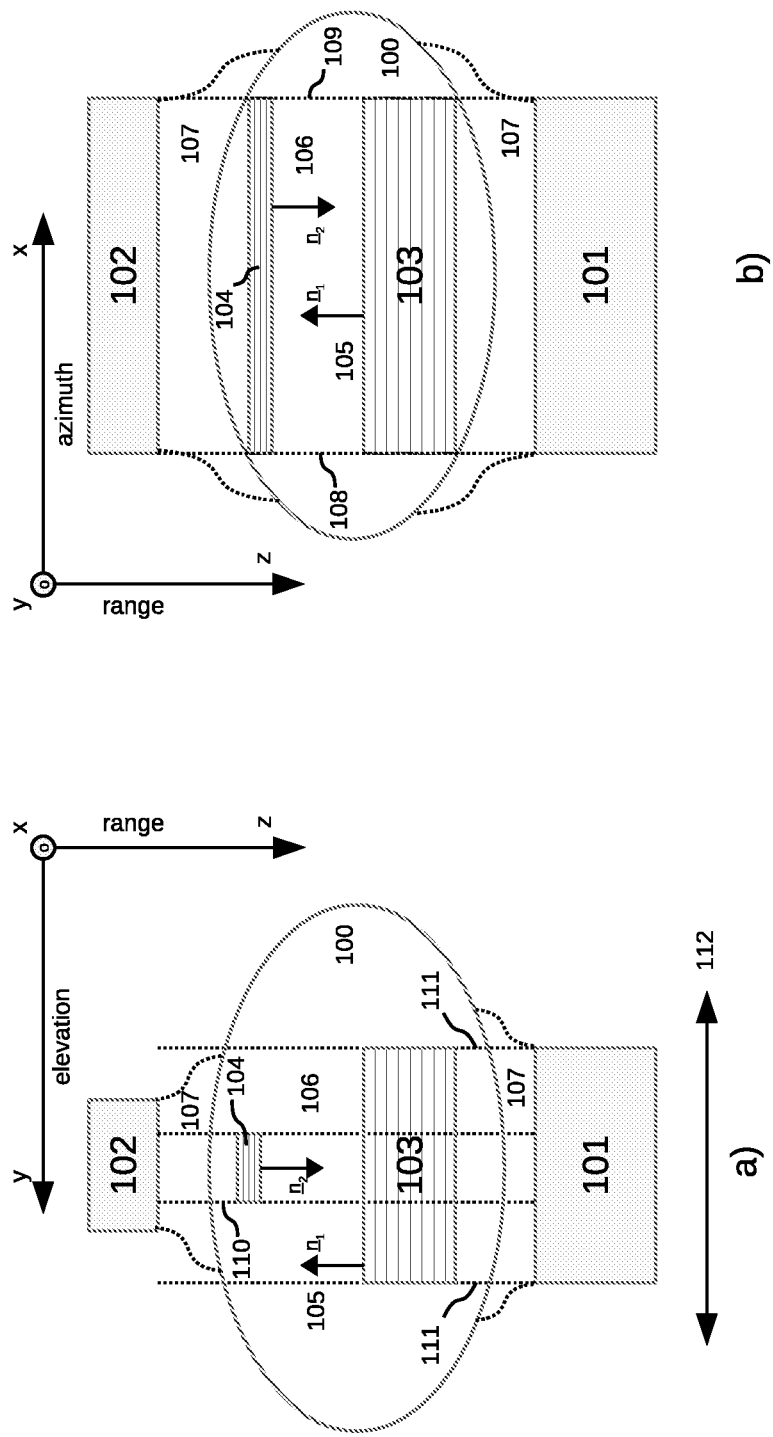
FIG. 4 illustrates a modification of the arrangement of arrays in FIG. 1, where the to beams propagate in opposite directions.

FIG. 4 shows another example embodiment according to the invention, which is a specialization of the embodiment in FIG. 1 with opposite direction ($\theta=\pi$) of the transmitted beams. The denominations are the same as in FIG. 1. The range of the overlap region is then $Z=(Z_1+Z_2)/2$, where $Z_1$ is the length of the pulse 103 and $Z_2$ is the length of the $2^{nd}$ pulse 104. To get a high range resolution in the image, we want a high frequency of the $2^{nd}$ transmit beam 104, with shortest possible pulse length $Z_2$. The length Z of the overlap-region, is then dominated by the length $Z_1$ of the $1^{st}$ transmitted pulse 103. The length of the overlap region can then be selected by the pulse length $Z_1$, while the range resolution is determined by the pulse length $Z_2$, and the location of the overlap region is selected by the relative timing between the $1^{st}$ and $2^{nd}$ transmit pulses.

The example embodiment in FIG. 4 is also useful with surface or plate waves in plate constructions to detect cracks in the plates, both as quality control in manufacturing and surveillance for safe operation of the structures. This has special interest with for example polymer composite structures in airplanes and other transport objects and windmills. To detect the presence of cracks from nonlinear interaction scattering, without detailed imaging of it, the receive beam could also be wide, where in principle the array 102 is composed of a single element. However, for electrical impedance matching to maximize receive signal to noise ratio it is convenient to divide also the receiver array into several elements. To obtain very wide waves at a distance from the arrays to cover a wide surface, on could also use an array to generate convex waves. One could in this situation use very simple beam formers, both for transmit and receive.

To get strong nonlinear scattering one wants as high amplitude of the $1^{st}$ transmitted pulse as possible, and this limits the pulse length to avoid over-heating of the transducer array and the tissue. We should note that with this arrangement of the arrays, the $1^{st}$ transmit pulse 103 will hit the receiver array 102 at the same time as the nonlinearly scattered signal components from Z which are much lower in amplitude. This can cause difficulties in adequate suppression of the receive components of the pulse 103 to show the nonlinear interaction scattering components with high sensitivity, especially with low difference between the frequency $f_1$ of pulse 103 and the nonlinear interaction components to be detected. The frequency selections described in FIG. 2c give a large difference between $f_1$ and the frequency components to be detected, and has advantages in this respect. This problem is reduced by allowing a small deviation of the angle $\theta$ between the beams from 180 deg ($\pi$) so that the $1^{st}$ pulse 103 hits the receive array 102 in a direction with low receive sensitivity or even passes outside the receive array 102. This gives some limitation of the overlap region near the transducer arrays, which can be made negligible by increasing the distance between the arrays and the object. To minimize this effect, the material around the arrays should be made highly absorbing of incoming effects.

Figure 5:
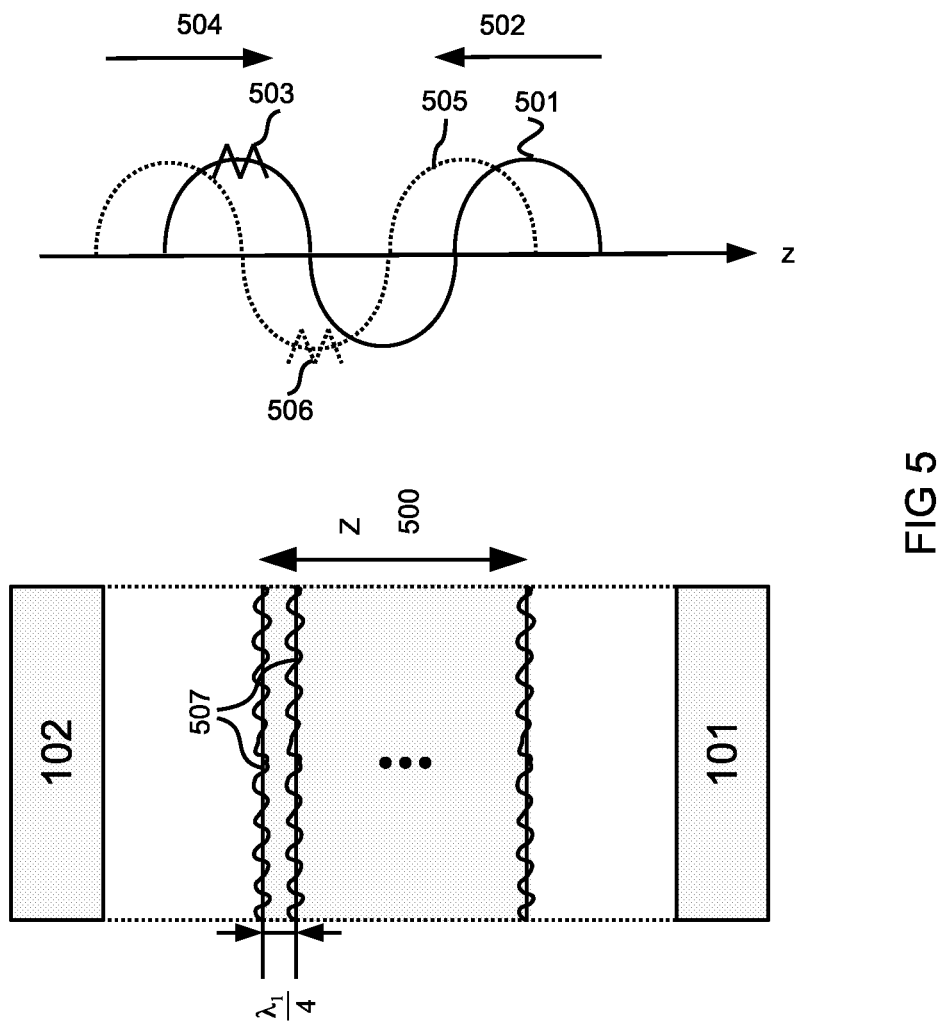
FIG. 5 illustrates nonlinear interaction scattering from opposite propagating waves when the center frequency of the $1^{st}$ transmitted wave is less than the temporal frequency bandwidth of the $2^{nd}$ transmitted wave.

When the manipulation pulse $p_1$ has much lower frequency than the imaging pulse $p_2$, as exemplified in FIG. 2c, the interaction scattering is strongest at the peaks of the LF oscillation, as illustrated in FIG. 5. In this Figure, 501 shows the LF pulse oscillation and 503 shows the HF pulse in a $1^{st}$ point in time, where the HF pulse is at the peak of the LF pulse oscillation. This peak LF pressure strongly produces a nonlinear change in the HF scattering. Using pulse inversion with two transmits where the LF pulse changes polarity, one is able to extract this nonlinear interaction scattering, around the peak oscillations of the LF pulse. Both the LF and the HF pulses propagate in their forward directions 502 and 504, respectively. After a time lag of $T_1/4$, where $T_1$ is the temporal period of the LF pulse, The LF pulse has moved forward $\lambda_1/4$, where $\lambda_1$ is the wave length of the LF pulse, to the location 505, while the HF pulse has moved forward in its direction to the location 506 at the trough of the LF pulse, which is a next depth of strong nonlinear interaction scattering between the LF and HF pulses. This corresponds to the analysis in relation to Eq. (5) with $\theta=\pi$. With pulse inversion of the LF pulse one is able retrieve the nonlinear interaction scattering also at this location of the pulses. The range distance between the locations of the HF pulses 503 and 506 is $\lambda_1/4$, where $\lambda_1$ is the wave length of the LF pulse. The nonlinear interaction scattered signal of the HF pulse is extracted using pulse inversion techniques.

With this method one hence gets regions of strong nonlinear interaction scattering with depth distance $\lambda_1/4$ within the whole overlap region, indicated as the lines 507 within the overlap region 500 in FIG. 5. If the distance between these lines is too large for the image resolution obtained with the short HF pulse, one can obtain fill in lines by a new image with small variations (e.g. $T_1/8$) between the transmit events of the HF and the LF pulse. One can also conveniently obtain an estimate of missing image points by interpolation between obtained image points.

The transmitted pulse amplitudes can be increased to increase the nonlinear interaction scattering by using overlapping, focused transmit pulses 103 and 104, and scanning said focused beams in the azimuth direction for 2D imaging, and both azimuth and elevation direction for 3D imaging, with adapted receive beam scanning, according to known methods. Elevation scanning for 3D imaging can be done by mechanical motion of the array structure as illustrated by the arrows 112 in FIGS. 1 and 4. With matrix arrays one can obtain electronic elevation scanning for 3D imaging with methods known in the art.

A block diagram of an instrument according to the invention is shown in FIG. 6, where the arrays 101 and 102 and the overlap region is described in relation to FIG. 1 and FIG. 3-5. The block 601 contains transmit beam formers for the $1^{st}$ and $2^{nd}$ pulsed beams for arrays 101 and 102, and also receive beam former for the element signals from the array 102. The beam formers operate according to known principles, for example transmission of focused or broad beams (e.g. plane wave imaging), and reconstruction of receive focused image data in the image points. The output of the receive beam former is transferred to a processing unit 602 that extracts the nonlinear interaction scattered signal, either through temporal filtering, pulse inversion methods, or a combination of the two. The processing unit is preferably set up to also extract the linearly scattered signal from the object separately according to known methods. From the processing unit the images are transferred to a display unit 603, where the nonlinear scattering components for example can be shown in a color code overlaying the linear scattering components typically in grey scale. All units take input and provide feedback data to a control unit 604 that takes input from user interface unit 606. The control unit can conveniently communicate with the other units via a bus system 605 according to known methods.

To provide maximal sensitivity to the frequency components in the nonlinear interaction scattered signal the scattered signal can also be picked up by a third array, for example illustrated as 607 in FIG. 6 that is positioned so that it can receive the nonlinear interaction scattered signal from the overlap region Z.

When the object can be completely surrounded by arrays, for example as with breast imaging, one can conveniently use a ring array known in the art for transmission of pulsed beams 103 and 104 where the direction of the beams are freely selectable by selecting the elements of the ring array used for the transmission. The ring array gives large flexibility for choosing the receive array aperture. This selection is convenient to provide spatial compounding of images obtained by different directions of the beams, known in the art. For transmission of pulses 103 and 104 that are widely separated in frequency as in FIG. 2c, one can use array structures as given in U.S. Pat. No. 7,727,156 or 8,182,428, which also are convenient for reception of frequency components in the high frequency band.

In FIGS. 1 and 3-5, the pulsed wave-fronts are illustrated as fairly straight lines, i.e. approximated by plane waves. In the practical situation, diffraction with the limited apertures make the wave fronts somewhat curved, especially at the edges of the beams. This can be accounted for in electronic receive beam forming. In FIGS. 4,5 we have illustrated that the $1^{st}$ and $2^{nd}$ transmit beams are in the same plane. This can be an advantage in many situations, as the depth location of the interaction region can be obtained through a variation of the transmit timing relation of the $1^{st}$ and $2^{nd}$ pulsed wave.

We have used ultrasound imaging as an example, but similar geometrical arrangements of transmitters and receivers can according to the invention also be used with EM waves. For EM imaging with frequencies in the GHz and THz range, the transmit means and receive means can be strip antennas or maser/laser diodes, and arrays of elements of these. For EM imaging in the infrared-optical frequency range, simple solutions for the transmit means are arrays of laser diodes, or mechanically direction steered laser diodes. Simple solutions for the receive detector means can be light sensing diodes/transistors or focused camera systems (e.g. a CCD camera) that provides real time imaging of the scattered signal from the whole interaction region. To further increase the sensitivity to the nonlinear interaction scattered signal, one can conveniently average the receive signal or image signal from many transmit events for each individual interaction region, according to known methods.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention.

It is also expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A method for measurement or imaging of nonlinear interaction scattering between two waves in a material object with nonlinear material parameters that produce wave scattering, comprising the steps of
    a) transmitting at least one transmit event comprising i) at least one $1^{st}$ transmit pulsed wave with a $1^{st}$ transmit time and a $1^{st}$ transmit center frequency along a $1^{st}$ transmit beam with a $1^{st}$ transmit direction, and ii) at least one $2^{nd}$ transmit pulsed wave with a $2^{nd}$ transmit time and a $2^{nd}$ transmit center frequency along a $2^{nd}$ transmit beam, where said 1st transmit beam and said 2nd transmit beam are oppositely directed and where said $1^{st}$ transmit beam crosses said $2^{nd}$ transmit beam in an elevation direction at an angle θ between the forward propagation directions of the beams where θ is an angle in the interval of 160-200 deg, wherein said angle θ is sufficiently different from 180 deg that one of, i) the 1st transmitted pulse hits the receive array at an angle with reduced sensitivity of the receive array, and ii) passes outside the receive array, and where the $1^{st}$ and $2^{nd}$ transmit beams and $1^{st}$ and $2^{nd}$ transmit times are arranged so that the pulses from the $1^{st}$ and $2^{nd}$ pulsed waves overlap in space in an overlap region Z,
    b) selecting one or both of i) the time relation between said $1^{st}$ and $2^{nd}$ transmit times, and ii) the pulse length of at least one of the $1^{st}$ and $2^{nd}$ transmit pulses, to control the depth location and dimension of said overlap region Z of nonlinear interaction between said $1^{st}$ and $2^{nd}$ pulsed waves that produces nonlinear interaction scattering within the object,
    c) receiving at least scattered wave components from the overlap region Z with at least one receiver and generating at least one receive signal that includes at least nonlinear interaction scattered signal components that relate to waves that are scattered from the nonlinear interaction between said $1^{st}$ and $2^{nd}$ pulsed waves in said overlap region, and
    d) processing said at least one receive signal to extract the nonlinear interaction scattered signal components to form nonlinear interaction measurement or image signals from said nonlinear interaction region.

2. A method for measurement or imaging according to claim 1, where the process to extract nonlinear interaction signal components includes temporal frequency filtering of the receive signal where said filtering passes said nonlinear interaction scattered signal components and blocks other temporal frequency components.

3. A method for measurement for imaging according to claim 1, where
    a) said transmitting step comprises at least two transmit events where said $1^{st}$ and $2^{nd}$ transmit beams and the time lag between said $1^{st}$ and $2^{nd}$ transmit times are the same for said at least two transmit events, and where
    b) one of said $1^{st}$ and $2^{nd}$ pulsed waves is varied in at least one of polarity, amplitude, phase and frequency between said at least two transmit events, including the possibility that at least one of said $1^{st}$ and $2^{nd}$ pulsed waves has zero amplitude for at least one of said transmit events, and where
    c) the process to extract nonlinear interaction scattering signal components includes combining of the receive signals from said at least two transmit events.

4. A method for measurement or imaging of nonlinear interaction scattering according to claim 3, where the center frequency of said $1^{st}$ pulsed wave is less than $1/3$ of the center frequency of said $2^{nd}$ pulsed wave.

5. A method for measurement or imaging of nonlinear interaction scattering according to claim 3, where at least one of the receive signals from said at least two transmit events are delay corrected before combining of the receive signals from said at least two transmit events.

6. A method for measurement or imaging of nonlinear interaction scattering according to claim 3, where the process to extract nonlinear interaction scattering signal components in addition includes temporal frequency filtering of the receive signal where said filtering passes said nonlinear interaction scattered signal components and blocks other temporal frequency components.

7. A method for measurement or imaging of nonlinear interaction scattering according to claim 1, where at least one of said $1^{st}$ and $2^{nd}$ transmit pulsed waves are essentially a plane wave.

8. A method for measurement or imaging of nonlinear interaction scattering according to claim 1, where at least one of said $1^{st}$ and $2^{nd}$ transmit pulsed waves are a focused wave.

9. A method according to claim 1, where at least a receive beam is scanned in one or both of i) an azimuth direction, and ii) an elevation direction to produce 2D and 3D images of the nonlinear interaction scattering.

10. An apparatus according to claim 1, where said transmit means transmits at least one of said $1^{st}$ and $2^{nd}$ transmit pulsed waves as essentially plane waves.

11. An apparatus according to claim 1, where said transmit means transmits at least one of said $1^{st}$ and $2^{nd}$ transmit pulsed waves as a focused wave.

12. An apparatus according to claim 1, where said processing means comprises means to average received signals from a plurality of transmit events for the same measurement or image region to reduce noise and improve sensitivity.

13. An apparatus according to claim 1, where said receive means comprises means to scan a receive beam in an azimuth direction to produce 2D images of the nonlinear interaction scattering.

14. An apparatus according to claim 1, where said receive means comprises means to scan a receive beam both in an azimuth and elevation direction to produce 3D images of the nonlinear interaction scattering.

15. An apparatus for measurement or imaging of nonlinear interaction scattering between two waves in a material object with nonlinear material parameters that produce wave scattering, comprising
   a) transmit means arranged to transmit at least one transmit event comprising i) at least one $1^{st}$ transmit pulsed wave with a $1^{st}$ transmit time and a $1^{st}$ transmit center frequency along a $1^{st}$ transmit beam with a $1^{st}$ transmit direction, and ii) at least one $2^{nd}$ transmit pulsed wave with a $2^{nd}$ transmit time and a $2^{nd}$ transmit center frequency along a $2^{nd}$ transmit beam, where said $1^{st}$ transmit beam and said $2^{nd}$ transmit beam are oppositely directed and where said $1^{st}$ transmit beam crosses said $2^{nd}$ transmit beam in the elevation direction at an angle θ between the forward propagation directions of the beams where θ is any angle in the interval of 160-200 deg and where θ is so much different from 180 deg that one of, i) the $1^{st}$ transmitted pulse hits the receive array at an angle with reduced sensitivity of the receive array, and ii) passes outside the receive array, and where the $1^{st}$ and $2^{nd}$ transmit beams and $1^{st}$ and $2^{nd}$ transmit times are arranged so that the pulses from the $1^{st}$ and $2^{nd}$ pulsed waves overlap in space in an overlap region Z,
   b) control means arranged to select one or both of i) the time relation between said $1^{st}$ and $2^{nd}$ transmit times, and ii) the pulse length of at least one of the $1^{st}$ and $2^{nd}$ transmit pulses, to control the depth location and dimension of said overlap region Z of nonlinear interaction between said $1^{st}$ and $2^{nd}$ pulsed waves that produces nonlinear interaction scattering within the object,
   c) receive means arranged to receive at least scattered wave components from the overlap region Z with at least one receiver and generating at least one receive signal that includes at least nonlinear interaction scattered signal components that relate to waves that are scattered from the nonlinear interaction between said $1^{st}$ and $2^{nd}$ pulsed waves in said overlap region, and
   d) processing means arranged to process said at least one receive signal to extract the nonlinear interaction scattered signal components and to form nonlinear interaction measurement or image signals from said nonlinear interaction region.

16. An apparatus according to claim 15, where said processing means comprises means for temporal frequency filtering of the receive signal where said filtering passes said nonlinear interaction scattered signal components and blocks other temporal frequency components.

17. An apparatus according to claim 15, where
   a) said transmit means is arranged to transmit at least two transmit events where said $1^{st}$ and $2^{nd}$ transmit beams and the time lag between said $1^{st}$ and $2^{nd}$ transmit times are the same for said at least two transmit events, and where
   b) said transmit means comprises means for varying at least one of polarity, amplitude, phase and frequency of one of said $1^{st}$ and $2^{nd}$ pulsed waves between said at least two transmit events, including the possibility that at least one of said $1^{st}$ and $2^{nd}$ pulsed waves has zero amplitude for at least one of said at least two transmit events, and where
   c) said processing means comprises means for combining the receive signals from at least two transmit events in the process of forming image signals in said overlap region.

18. An apparatus according to claim 17, where said transmit means comprises means to transmit said $1^{st}$ pulsed wave with a center frequency less than $1/3$ of the center frequency of said $2^{nd}$ pulsed wave.

19. An apparatus according to claim 17, where said processing means is arranged for delay correcting at least one of the receive signals from said at least two transmit events before combining the receive signals from said at least two transmit events.

20. An apparatus according to claim 17, where said processing means comprises means that in addition includes temporal frequency filtering of the receive signal where said filtering passes said nonlinear interaction scattered signal components and blocks other temporal frequency components.

21. An apparatus according to claim 15, where at least one of said $1^{st}$ and $2^{nd}$ pulsed waves is an elastic compression wave.

22. An apparatus according to claim 15, where at least one of said $1^{st}$ and $2^{nd}$ pulsed waves is an elastic shear wave.

23. An apparatus according to claim 15, where at least one of said $1^{st}$ and $2^{nd}$ pulsed waves is an electromagnetic wave.

24. An apparatus according to claim 21, where said receive means is a focused camera.

\* \* \* \* \*